(12) United States Patent
Oberlaender et al.

(10) Patent No.: US 7,749,236 B2
(45) Date of Patent: Jul. 6, 2010

(54) DEVICE FOR GUIDING SURGICAL SEWING MATERIAL TO A NEEDLE

(75) Inventors: Martin Oberlaender, Engen (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 610 days.

(21) Appl. No.: 11/399,189

(22) Filed: Apr. 6, 2006

(65) Prior Publication Data

US 2006/0229642 A1  Oct. 12, 2006

(30) Foreign Application Priority Data

Apr. 6, 2005  (DE) .................. 10 2005 015 687

(51) Int. Cl.
 *A61B 17/04* (2006.01)
(52) U.S. Cl. ..................................... 606/148
(58) Field of Classification Search ......... 606/139–150; 81/52, 53.12; 433/117–119; 289/17; 132/309
See application file for complete search history.

(56) References Cited

U.S. PATENT DOCUMENTS

| 373,372 | A | * | 11/1887 | La Forest King | 606/146 |
|---|---|---|---|---|---|
| 919,138 | A | | 4/1909 | Drake et al. | 606/144 |
| 962,218 | A | | 6/1910 | Heitz-Boyer | |
| 1,180,975 | A | | 4/1916 | Chapman | |
| 1,270,639 | A | * | 6/1918 | Malcom | 223/104 |
| 2,008,251 | A | | 7/1935 | Hillebrand | 128/339 |
| 2,474,463 | A | * | 6/1949 | Burrell | 242/129.53 |
| 2,744,463 | A | | 5/1956 | Keefe | 242/129.53 |
| 2,808,055 | A | | 10/1957 | Thayer | 128/340 |
| 3,013,559 | A | * | 12/1961 | Thomas | 606/146 |
| 3,186,262 | A | * | 6/1965 | Parstorfer | 140/93 R |
| 3,840,017 | A | * | 10/1974 | Violante | 606/146 |
| 4,012,010 | A | | 3/1977 | Friedman | 242/129.8 |
| 5,405,354 | A | * | 4/1995 | Sarrett | 606/148 |
| 5,454,821 | A | * | 10/1995 | Harm et al. | 606/148 |
| 5,776,151 | A | | 7/1998 | Chan | 606/148 |
| 5,919,199 | A | * | 7/1999 | Mers Kelly et al. | 606/139 |

(Continued)

FOREIGN PATENT DOCUMENTS

DE  73 10 005 U1  3/1973

(Continued)

OTHER PUBLICATIONS

European Search Report, Aug. 8, 2006, 6 pages.

(Continued)

*Primary Examiner*—(Jackie) Tan-Uyen T Ho
*Assistant Examiner*—Son Dang
(74) *Attorney, Agent, or Firm*—St. Onge Steward Johnston & Reens LLC

(57) ABSTRACT

The invention relates to a device for guiding surgical sewing material to a needle, having a shaft on whose distal end the needle can be secured and whose proximal end is configured as a gripping portion equipped with an open guide channel for the sewing material that is to be guided. To create a device that is of simple construction and ensures reliable transport of the sewing material to the needle, the invention proposes that the guide channel can be locked mechanically, at least in sections.

12 Claims, 2 Drawing Sheets

U.S. PATENT DOCUMENTS

| | | | | |
|---|---|---|---|---|
| 5,944,724 A * | 8/1999 | Lizardi | ................ | 606/104 |
| 6,780,198 B1 * | 8/2004 | Gregoire et al. | ............ | 606/232 |
| 7,311,715 B2 * | 12/2007 | Sauer et al. | ................ | 606/148 |
| 7,416,556 B2 * | 8/2008 | Jackson | ................ | 606/232 |
| 2003/0109891 A1 * | 6/2003 | Dana et al. | ................ | 606/148 |
| 2003/0114864 A1 * | 6/2003 | McRury et al. | ............ | 606/148 |
| 2003/0167990 A1 * | 9/2003 | Lee et al. | ................ | 112/231 |
| 2005/0090841 A1 * | 4/2005 | Morrison | ................ | 606/148 |
| 2005/0125009 A1 * | 6/2005 | Perry et al. | ............... | 606/139 |
| 2005/0165417 A1 * | 7/2005 | Sauer et al. | ................ | 606/144 |
| 2005/0277957 A1 * | 12/2005 | Kuhns et al. | ................ | 606/148 |
| 2005/0283171 A1 * | 12/2005 | Bellafiore et al. | ............ | 606/144 |
| 2006/0000316 A1 * | 1/2006 | Hsieh | ................ | 81/52 |
| 2008/0033460 A1 * | 2/2008 | Ziniti et al. | ................ | 606/148 |

FOREIGN PATENT DOCUMENTS

DE     2 257 728     4/1974

OTHER PUBLICATIONS

German Office Action, Dec. 22, 2005, 4 pages.

\* cited by examiner

DEVICE FOR GUIDING SURGICAL SEWING MATERIAL TO A NEEDLE

CROSS-REFERENCE TO RELATED APPLICATIONS

The present application claims priority of German patent application No. 10 2005 015 687.8 filed on Apr. 6, 2005, the content of which is incorporated herein by reference.

FIELD OF THE INVENTION

The invention relates to a device for guiding surgical sewing material to a needle, having a shaft on whose distal end the needle can be secured and whose proximal end is configured as a gripping portion equipped with an open guide channel for the sewing material that is to be guided.

BACKGROUND OF THE INVENTION

Devices of this type serve to guide the surgical sewing material, starting from a spool of thread, to a surgical needle configured as a rule at least partly as a hollow needle.

U.S. Pat. No. 2,808,055 describes a device for guiding surgical sewing material that consists of a gripping portion and a transport device positioned in the gripping portion, by means of which the sewing material can be guided to the needle by forward and backward sliding of a glide shoe. The disadvantage of this known guide device is the fact that the construction of the transport device is very large and in addition operation of the transport device requires some practice.

A generic device, of simpler construction, for guiding surgical sewing material to a needle that has no separate transport device is known in practice. This well-known device consists essentially of a shaft, on whose distal end the needle can be secured, and whose proximal end is configured as a gripping portion equipped with an open guide channel for the sewing material that is to be guided. The sewing material, contained in the guide channel, is guided to the needle by continued sliding of additional sewing material through the proximal end of the shaft into the guide channel. This otherwise very reliable device has the disadvantage that the sewing material pushed forward toward the needle, because of its own stiffness, tends to pile up and to protrude upward out of the guide channel as soon as a slightly greater resistance occurs in the forward area of the sewing material, for instance when it is introduced into the needle. However, as soon as the sewing material protrudes out of the guide channel, further advancement of the sewing material toward the needle is impossible.

On the basis of this situation, it is the aim of the invention to create a device for guiding surgical sewing material to a needle that is of simple construction and ensures reliable transport of the sewing material to the needle.

SUMMARY OF THE INVENTION

This aim is achieved according to the invention in such a way that the guide channel can be mechanically locked, at least in sections.

Because the invention proposes to design the guide channel so that it can be mechanically locked, at least in sections, the piling up and protrusion of the sewing material out of the guide channel is prevented. Because of the natural stiffness of the sewing material, it is sufficient to lock the guide channel only in some portions. The remaining area between two locked areas of the channel can be designed so that repeated piling up of the sewing material is prevented.

According to a first embodiment of the invention, it is proposed that at least one locking element retaining the sewing material in the guide channel should be installed to lock the guide channel.

It is proposed with a preferred embodiment of the invention that the at least one locking element should have at least one blocking element to lock the guide channel above the sewing material, at least in sections, This blocking element positioned above the sewing material blocks any possible piling up of the sewing material and thus allows additional forward and reverse pushing of the sewing material along the guide channel. Every locking element advantageously has two blocking elements that are contiguous to one another.

The invention proposes, for the configuration of the blocking elements, that they should preferably be configured as O-rings consisting of a plastic or rubber material. Configuring the blocking elements as two contiguous O-rings of an elastic material, such as a plastic or rubber material for instance, has the advantage that the sewing material can be pressed from above between the mutually contiguous blocking elements forward into the guide channel, without being obliged to open the lock element and/or the blocking element in a separate operational step.

It is also proposed with the invention that every locking element is configured as a threaded bolt that can be screwed into the gripping portion from the side opposite the guide channel, and in the shaft of said bolt a groove is configured that corresponds to the guide channel, so that according to the invention the blocking elements are positioned on the free ends of the shaft that is divided in two by the groove.

To ensure that the groove configured in the shaft of the screwing bolt can always be aligned flush with the guide channel configured in the gripping portion of the device, the shaft with the groove is positioned so that it can rotate freely on the threaded bolt.

It can be made easier to insert the threaded bolt correctly aligned into the gripping portion if, on the rotatable shaft, at least one positioning element is configured that interacts with a corresponding positioning element in the gripping portion. The positioning element configured on the rotatable shaft is advantageously configured as a longitudinal rib, which can be inserted into a corresponding longitudinal groove in the gripping portion so that an even alignment of the groove and the guide channel is constantly ensured.

According to a second embodiment of the invention, it is proposed that to lock the guide channel, the guide channel can be covered at least in sections by means of a locking device. Alternatively to the positioning of a locking element inside the guide channel, in this embodiment the guide channel is covered on its surface by means of at least one appropriate locking device.

To form this locking device that covers the guide channel, it is proposed, according to a first constructive embodiment of the invention, that the locking device is configured as a covering lid positioned on the gripping portion.

According to an alternative embodiment, the locking device is configured as a clamp that can be secured on the gripping portion of the device and that preferably is configured as a spring element surrounding the gripping portion. Owing to the configuration of the clamp as a spring element, the clamp can be set simply onto the gripping portion.

With an additional embodiment of the locking device it is proposed that the device is configured as a slidable sleeve that can be essentially form-fitted onto the gripping portion.

It is further proposed with the invention that on the distal end of the gripping portion a gripping hollow is configured for clamped gripping of the sewing material. The gripping hollow here is configured in such a way that it is adjusted to the position and shape of the thumb of the hand holding the device. Holding the sewing material so that it is at times clamped is advantageous in order to prevent unintentionally pulling the sewing material out of the needle.

Finally, it is proposed with the invention that on the floor of the gripping hollow a guide groove is configured to insert the sewing material, first in order to hold the sewing material in the correct alignment even with clamped gripping of the sewing material, and second in order to prevent kinks in the sewing material.

Additional characteristics and advantages of the invention can be seen with reference to the associated illustrations, which depict, in merely exemplary fashion, three embodiments of a device according to this invention for guiding surgical sewing material to a needle.

DETAILED DESCRIPTION OF THE INVENTION

Figure 1:
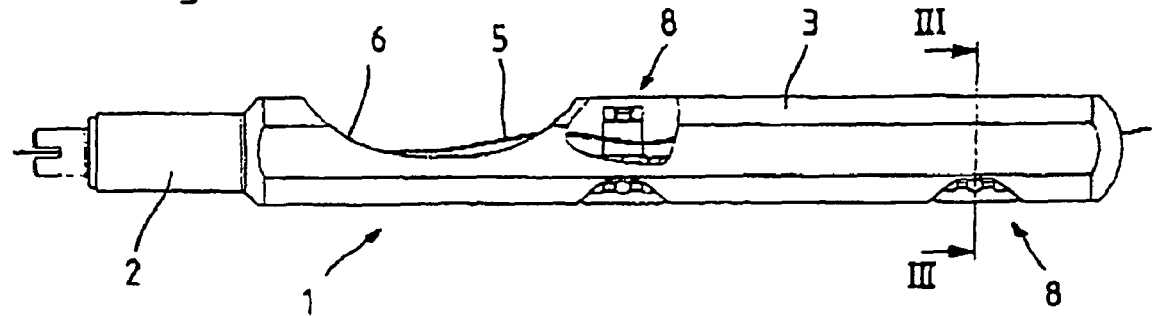
FIG. 1 shows a partially cutaway side view of a first embodiment of a device according to the invention.

The device shown in the illustrations for guiding surgical sewing material to a needle consists essentially of a shaft 1, on whose distal end a surgical needle (not illustrated), especially a hollow needle equipped with a bored through-hole, can be secured by an adapter piece 2. The proximal end of the shaft 1 is shaped as a gripping portion 3 in which is configured a guide channel 4, running in the longitudinal direction of the shaft 1, to receive and guide the sewing material 5.

Figure 2:
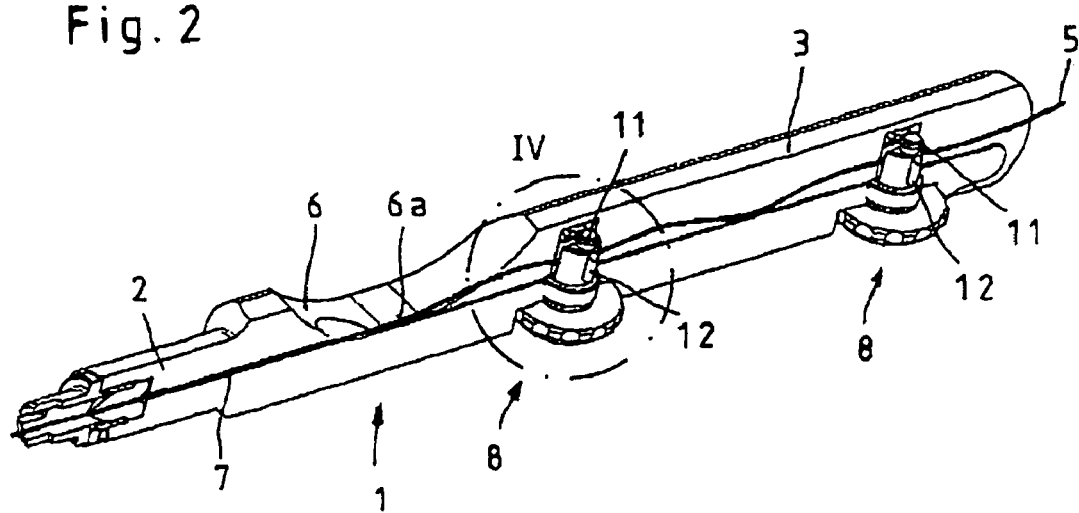
FIG. 2 shows a perspective longitudinal section through the device shown in FIG. 1.
Figure 3:
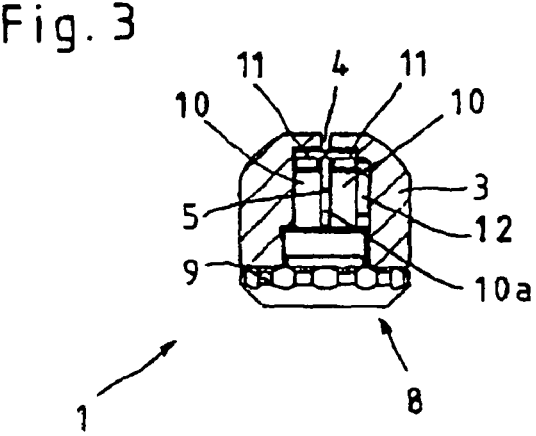
FIG. 3 shows an enlarged section along the line III-III according to FIG. 1.
Figure 4:
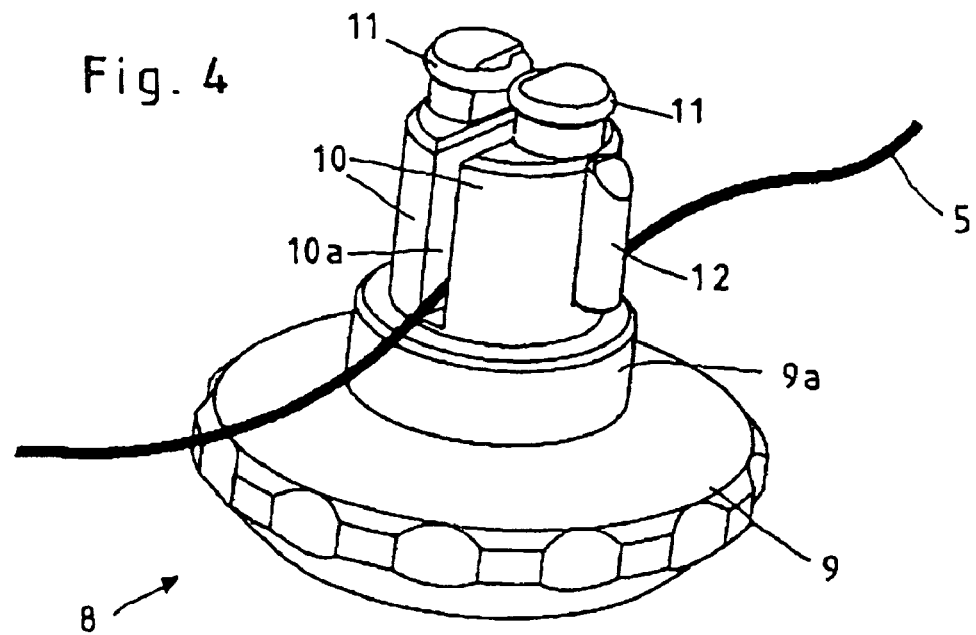
FIG. 4 shows an enlarged perspective view of detail IV according to FIG. 2.
Figure 5:
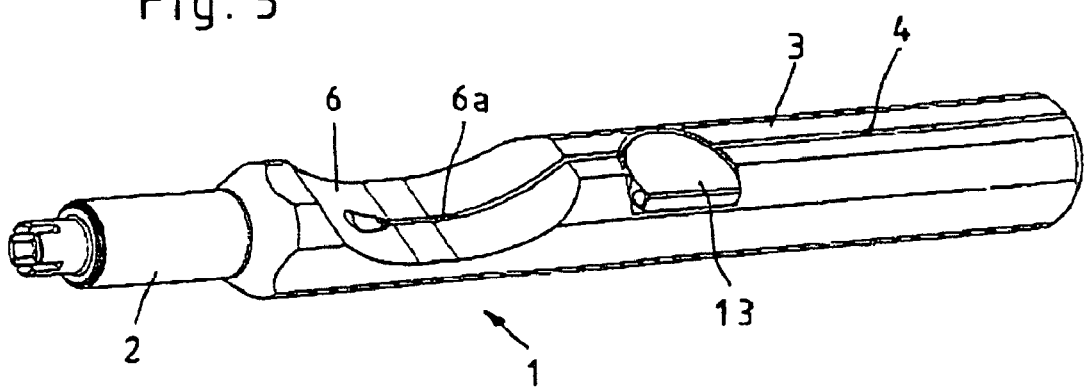
FIG. 5 shows a perspective side view of a second embodiment of a device according to the invention.

As can be further seen from FIGS. 1, 2, and 5, on the distal end of the gripping portion 3, that is, in the area of the shaft 1 between the gripping portion 3 and the adapter piece 2, a gripping hollow 6 is configured, which in position and shape is adapted so that it serves to insert the thumb of the hand holding the shaft 1.

To prevent the sewing material 5, positioned in the guide channel 4, which is to be guided to the needle by means of a bored through-hole 7 in the adapter piece 2, from protruding out of the guide channel 4 when sewing material 5 is advanced through the proximal end of the shaft 1 and from piling up out of the guide channel 4 because of the stiffness of the sewing material 5, as soon as a certain resistance occurs on the distal side, for instance in threading the needle, mechanical means are provided so that the guide channel 4 can be locked at least in sections.

In the first embodiment shown in FIGS. 1 to 4, this locking of the guide channel 4 is performed by two locking elements 8 positioned in the guide channel 4, by means of which elements the sewing material 5 can be held on the guide channel 4. As can be seen in particular from FIGS. 2 and 4, the locking elements 8 are configured as threaded bolts that can screw into the gripping portion 3 of the shaft 1 from the side opposite the opening of the guide channel 4. The threaded bolt that forms the locking element 8 consists here essentially of a base body 9 equipped with an outer thread 9a as well as a shaft 10 that is positioned so that it can rotate freely on the base body 9 and that is divided into two shaft shanks by a vertical groove 10a corresponding to the guide channel 4.

The sewing material 5 is actually retained in the guide channel 4 or in the groove 10a of the shaft 10 by means of blocking elements 11 positioned on the free ends of the shaft shanks, which blocking elements in the illustrated embodiment are configured as two mutually contiguous O-rings, which consist of a plastic or rubber material. As is seen in particular in the sectional drawing of FIG. 3, the two mutually contiguous O-ring blocking elements 11 lock the groove 10a configured in the shaft 10 of the locking element 8 and thus also the guide channel 4 in such a way, that the sewing material arranged in the guide channel 4 and the groove 10a cannot protrude upward out of the guide channel 4 simply by piling up.

To facilitate proper alignment of the locking elements 8 in the gripping portion 3 of the shaft 1, in which the groove 10a is flush with the guide channel 4, on the shaft 10, in addition to the rotatable positioning of the shaft 10 on the base body 9, a positioning element 12 is configured, which in the illustrated embodiment has the shape of a longitudinal rib and interacts with a corresponding longitudinal groove (not illustrated) in the gripping portion 3.

Figure 6:
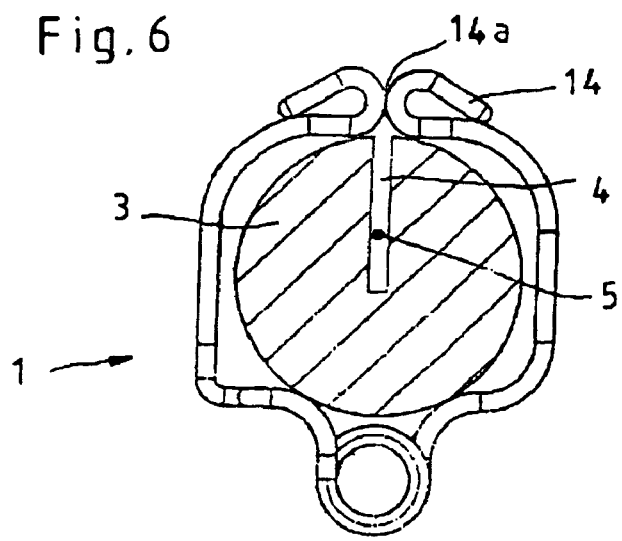
FIG. 6 shows a third embodiment of a device according to the invention, in cross-section.

In the two embodiments illustrated in FIGS. 5 and 6, the mechanical locking of the guide channel 4 occurs because the guide channel 4 configured in the gripping portion 3 and open at the top can be covered, at least in sections, by means of a locking device.

According to the second embodiment, illustrated in FIG. 5, this locking element is configured as a covering lid 13 rotatably mounted on the gripping portion 3. To insert the sewing material 5 into the guide channel 4, the covering lid 13 is flipped open and the sewing material 5 is inserted from above into the guide channel 4. During operation the covering flap 13 is held in the locked position by the user's hand, which grips around the shaft 1 of the device, so that any unintentional protrusion of the sewing material 5 out of the guide channel 4 is prevented. According to an alternative embodiment the covering lid 13 can also be configured in such a way that it is pre-weighted by a spring element in the closing direction so that the covering lid 13 is configured as a self-securing snapping device.

In the third embodiment, illustrated in FIG. 6, the covering of the guide channel 4 is ensured by a clamp 14 that can be secured on the gripping portion 3 and surrounds it and, as illustrated, can be configured as a spring element. Alternatively to the configuration as a clamp 14, it is possible to configure the covering as a sleeve that is essentially form-fitted and can slide onto the gripping portion 3. The clamp 14 or the sleeve, after insertion of the sewing material 5 into the guide channel 4, is mounted on the gripping portion 3 of the shaft 1 in order to lock the guide channel 4 on its surface and to prevent unintentional protrusion of the sewing material 5 out of the guide channel 4. In the case of the clamp 14, however, it is also possible to apply it on the gripping portion 3 of the shaft 1 before the insertion of the sewing material 5 into the guide channel 4 and to guide the sewing material 5 into the guide channel 4 through an opening 14a of the clamp 14 positioned essentially flush with the guide channel 4.

The use of the device for guiding surgical sewing material 5 to a needle is described hereafter with reference to the embodiment illustrated in FIGS. 1 to 4.

To start, the surgical needle to be equipped with the sewing material 5 is secured on the adapter piece 2 of the shaft 1 of the device.

Then the sewing material 5 is inserted from above into the guide channel 4 that is open at the top until this material reaches the blocking element 11 of the two locking elements 8 positioned in the guide channel 4. Because the two mutually contiguous blocking elements 11 configured as O-rings consist of an elastic plastic or rubber material, it is possible to press the sewing material 4 from above through the two mutually contiguous blocking elements 11 so that the sewing material 5 comes to rest in the area of the locking element 8 inside the groove 10*a*.

Hereafter the sewing material 5 is threaded into the bored through-hole 7 and, by sliding the sewing material 5 over the proximal end of the shaft 1, this material 5 is pushed forward in the distal direction until it again emerges from the needle secured on the adapter piece 2. It is also possible, of course, to thread the sewing material 5 ahead of time into the bored through-hole 7, that is, before the sewing material 5 is pressed through the blocking elements 11.

By means of the blocking elements 11 of the locking elements 8, the sewing material 5 is prevented from piling up and from protruding from the guide channel 4 as soon as a resistance occurs upon pushing forward the sewing material on the distal side. Upon insertion of the sewing material 5 into the guide channel 4 and the grooves 10*a*, the sewing material 5 allows itself to be pressed through between the blocking elements 11 because of the flexibility of the material of the blocking elements 11, but these blocking elements 11 prevent the sewing material 5 from protruding because the pressure force arising in normal operation when sewing material 5 is pushed forward is not so great as to allow the clamping force of the blocking elements 11 to be overcome.

The gripping hollow 6 configured in the area between the adapter piece 2 and the gripping portion 3 in the shaft 1 serves, during activation of the device, to allow the sewing material 5 to be gripped by clamping in order to prevent the sewing material 5 from being pulled out of the needle. In order, first, to hold the sewing material 5 in the correct alignment to the needle even during clamped gripping of the sewing material and, second, to prevent kinks in the sewing material 5, a guide groove 6*a* is configured on the floor of the gripping hollow 6.

The device for guiding surgical sewing material 5 to a needle, configured in this manner, is distinguished by the fact that the device, along with simple construction and simple handling, ensures reliable transport of the sewing material 5 to the needle.

What is claimed is:

1. A device for guiding surgical sewing material to a needle, having a shaft on whose distal end a needle can be secured and whose proximal end is configured as a gripping portion equipped with an open guide channel for the sewing material that is to be guided, wherein the guide channel can be mechanically locked, at least in sections by means of at least one locking element configured in the guide channel, distinguished in that the at least one locking element has two blocking elements that are contiguous with one another and that, at least in sections, lock the guide channel above the sewing material, so that the sewing material can be pressed from above into the guide channel, and distinguished in that that every locking element is configured as a threaded bolt that can be screwed into the gripping portion from the side opposite the guide channel, and in the shaft of this threaded bolt a guiding groove is configured corresponding to the guide channel, such that the shaft can rotate freely on the threaded bolt.

2. A device according to claim 1, distinguished in that the at least one blocking element is configured as an O-ring consisting of a plastic or rubber material.

3. A device according to claim 1, distinguished in that the blocking elements are positioned on the free ends of the shaft of the threaded bolt divided in half by the groove.

4. A device according to claim 1, distinguished in that on the rotatable shaft at least one positioning element is configured, which interacts with a corresponding positioning element in the gripping portion.

5. A device according to claim 4, distinguished in that the positioning element configured on the rotatable shaft is configured as a longitudinal rib, which can be inserted into a corresponding longitudinal groove in the gripping portion.

6. A device according to claim 1, distinguished in that the guide channel can be covered at least in sections by means of at least one locking device.

7. A device according to claim 6, distinguished in that the locking device is configured as a covering lid positioned on the gripping portion.

8. A device according to claim 6, distinguished in that the locking device is configured as a clamp that can be secured on the gripping portion.

9. A device according to claim 8, distinguished in that the clamp is configured as a spring element surrounding the gripping portion.

10. A device according to claim 6, distinguished in that the locking device is configured as a sleeve that can be slid onto the gripping portion.

11. A device according to claim 1, distinguished in that a gripping hollow is configured on the distal end of the gripping portion in the shaft for clamped gripping of the sewing material.

12. A device according to claim 6, distinguished in that a guide groove is configured on the floor of the gripping hollow to receive the sewing material.

* * * * *